(12) United States Patent
Nick et al.

(10) Patent No.: US 7,947,673 B2
(45) Date of Patent: May 24, 2011

(54) METHOD OF SCINTIGRAPHY

(75) Inventors: Hanspeter Nick, Duggingen (CH); Rene Lattmann, Oberwil (CH)

(73) Assignee: Novartis AG, Basel (CH)

( * ) Notice: Subject to any disclaimer, the term of this patent is extended or adjusted under 35 U.S.C. 154(b) by 483 days.

(21) Appl. No.: 12/091,970

(22) PCT Filed: Oct. 30, 2006

(86) PCT No.: PCT/EP2006/067916
§ 371 (c)(1),
(2), (4) Date: Apr. 29, 2008

(87) PCT Pub. No.: WO2007/051773
PCT Pub. Date: May 10, 2007

(65) Prior Publication Data
US 2008/0279962 A1 Nov. 13, 2008

Related U.S. Application Data

(60) Provisional application No. 60/746,784, filed on May 9, 2006.

(30) Foreign Application Priority Data

Nov. 1, 2005 (GB) .................................. 0522302.9

(51) Int. Cl.
*A61K 31/555* (2006.01)
*C07D 249/08* (2006.01)
(52) U.S. Cl. ....................................... 514/184; 548/106
(58) Field of Classification Search ................... 514/184; 548/106
See application file for complete search history.

(56) References Cited

U.S. PATENT DOCUMENTS

| 5,618,838 | A | 4/1997 | Chevion et al. |
| 6,558,650 | B1 | 5/2003 | Morton et al. |
| 6,602,989 | B1 | 8/2003 | Sadik et al. |

FOREIGN PATENT DOCUMENTS

| WO | 97/49395 | 12/1997 |
| WO | WO 97/49395 | * 12/1997 |
| WO | 03/039541 | 5/2003 |
| WO | 2005/097062 | 10/2005 |

OTHER PUBLICATIONS

Steinhauser et al. "Complex Formation of ICL670 and Related Ligands with Fe III and Fe II" European Journal of Inorganic Chemistry, 2004, pp. 4177-4192.*
Database Open Drug Database, Sep. 2005, Novartis Pharma Schweiz AG: "Exjade" XP002420619.
Kontoghiorghes, G.J. et al. "The Design and Development of Deferiprone (I1) and Other Iron Chelators for Clinical Use: Targeting Methods and Application Prospects", Current Medicinal Chemistry, vol. 11, No. 16, pp. 2161-2183, (2004).
Lundberg, J.H. et al. "Interaction of Gallium Nitrate with Fludarabine and Iron Chelators Effects on the Proliferation of Human Leukemic HL60 Cells", Biosis, (1990).
Richardson D. R. et al. "The Potential of Iron Chelators of the Pyridoxal Isonicotinoyl Hydrazone Class as Effective Antiproliferative Agents", Blood, vol. 86, No. 11, pp. 4295-4306 (1995).
Seligman P et al. "treatment with Fallium Nitrate: Evidence for Interference with Iron Methabolish in Vivo", American Journal of Hematology, vol. 41, No. 4, pp. 232-240 (1992).
Arion v.B et al. Synthesis, Structure, Spectroscopic amnd in Vitro antitumour Studies of a Novel galliium (III) Complex with 2-Acetylpyridine, vol. 91, No. 1, pp. 298-305, (2002).
Steinhauser S et al. "Complex Formation of ICL670 and Related ligands with $Fe^{III}$ and $Fe^{II}$".

* cited by examiner

Primary Examiner — Joseph R Kosack
(74) Attorney, Agent, or Firm — Gregory C. Houghton

(57) ABSTRACT

The invention relates to combination comprising a pharmaceutically acceptable preparation of a compound of formula (I), or a pharmaceutically acceptable salt thereof, and a gallium and its use in diagnosis. The invention also pertains to the use of a compound of formula I or a pharmaceutically acceptable salt thereof, for the preparation of a medicament for the treatment of an excess iron overload in the human or animal body whereby said body is undergoing gallium scintigraphy and whereby the treatment removing said excess of iron is interrupted for a period of 2 to 10 days prior to the gallium scintigraphy and resumed after the gallium scintigraphy readings.

(I)

2 Claims, No Drawings

METHOD OF SCINTIGRAPHY

This application claims priority from Great Britain Application No. 0522302.9 filed Nov. 1, 2005 and claims benefit of U.S. Provisional Application No. 60/746,784, filed May 9, 2006, which in their entirety are herein incorporated by reference.

FIELD OF THE INVENTION

The present invention relates to a diagnostic method using gallium when applied to patients undergoing Compound of formula I, or a pharmaceutically acceptable salt thereof treatment. The invention also relates to the use of Compound of formula I or a pharmaceutically acceptable salt thereof, for the preparation of a medicament for the treatment of iron overload, characterized in that said treatment is to be interrupted when the patient is undergoing scintigraphy, especially scintigraphy based on gallium 67. The present invention further relates to a combination comprising a gallium uptake enhancer such as a Compound of formula I, or a pharmaceutically acceptable salt thereof and a gallium, and to its uses. The invention pertains to a method of increasing the uptake of gallium into organs, especially highly perfused organs, such as the liver, lungs, heart, kidney and brain, for diagnostic and/or therapeutic purposes. The present invention also relates to a complex of gallium and a gallium uptake enhancer.

BACKGROUND OF THE INVENTION

The treatment of iron overload is in particular indicated in transfusion dependent anemias, in particular thalassemia major, thalassemia intermediate and in sickle cell disease to reduce iron-related morbidity and mortality, as well as in the treatment of hemochromatosis.

Clinical thalassemia (major and intermedia) are hereditary disorders characterized by defective production of hemoglobin, which leads to decreased production and increased destruction of red blood cells.

Sickle cell disease is caused by a mutation in the hemoglobin-Beta gene leading to the production of abnormal hemoglobin S. Normal red blood cells die after 120 days and sickle cells (red blood cells with hemoglobin S) are destroyed more rapidly (10 to 20 days) causing anemia. This anemia is what gives the disease its commonly known name—sickle cell anemia.

Hemochromatosis, the most common form of iron overload disease, is an inherited disorder that causes the body to absorb and store too much iron. The extra iron builds up in organs and damages them. Without treatment, the disease can cause these organs to fail.

Patients with sickle cell disease or thalassemia, who receive significant numbers of blood transfusions and patients with hemochromatosis require therapy to remove iron from the body, called chelation therapy.

The International Patent Publication WO 97/49395 discloses substituted 3,5-diphenyl-1,2,4-triazoles in the free acid form, salts thereof and its crystalline forms useful for the treatment of iron overload, which are hereby incorporated by reference. The International Patent Publications WO 2004/035026 and WO2005/097062 disclose particular advantageous pharmaceutical preparations in the form of dispersible tablets, which are hereby incorporated by reference.

Gallium (Ga), a Group IIIa transition metal, has a number of isotopes with many medical uses. For decades, gallium-67, a gamma-emitter, has been used in nuclear medicine for tumor imaging by gamma emission scintigraphy. Other isotopes of gallium have potential uses in oncology. Gallium-68, a positron emitter, can be used for tumor imaging by positron emission tomography (PET). Gallium-72, a beta-emitter, may destroy tissues that concentrate gallium by local radiation. This treatment has been proposed to palliate bone pain caused by skeletal metastases, e.g. in Andrews G A et al. Radiology 61: 570-588, 1953.

The "gallium compound" or "gallium" or "Ga" may be, for example, gallium nitrate, gallium citrate or gallium chloride. Examples of the gallium metal or isotope are Ga-67, Ga-68, Ga-69, Ga-71 and Ga-72 (where Ga-69 and 71 are stable isotopes, and the others are unstable radioactive isotopes).

Stable, e.g. non-radioactive, gallium has been used to reduce the hypercalcemia of malignancy, and as a treatment for Paget's disease of bone. It is also believed to have direct anti-neoplastic effects, and is currently under investigation as an adjunct to conventional chemotherapy, e.g. Chitambar C R et al. Cancer Research 54: 3224-3228, 1994; Seligman P A et al. Blood 82: 1608-1617, 1993; Chitambar C R et al. Am J Clin Oncol 20: 173-178, 1997.

The limitations of Ga-67 for oncologic imaging are well-recognized, e.g. in Tzen K Y et al. J Nucl Med 5: 327-332, 1980, Tsan, M F. J. Nucl. Med. 26: 89-92, 1985, Merz T et al. Cancer Res. 34: 2495-2499, 1974, Anghileri L J et al. Oncology 34: 74-77, 1977.

Many tumors accumulate Ga poorly. Others, such as hepatomas and lymphomas, can be intensely Ga-avid but may vary in magnitude and consistency of uptake. Delineation of tumors from background tissues often requires extended intervals from the time of injection to imaging of 3-7 days or more because Ga-67 localizes slowly and initial images of the abdomen are frequently difficult to interpret because of bowel activity. Because of the extended intervals required for oncologic imaging, a relatively high dose of Ga-67 is required, e.g. typically 10 mCi for an adult.

Despite years of imaging experience with Ga-67, the mechanism by which Ga-67 accumulates in normal tissues and tumors remains controversial.

Scintigraphy, in particular scintigraphy based on gallium 67, is a useful diagnostic technique for detecting diseases.

In particular, gallium citrate 67, also known under the tradename Neoscan®, Medi-Physics, Inc., Amersham Healthcare, is used in the diagnosis of neoplastic diseases, e.g. to detect primary and metastatic tumors, e.g. to demonstrate the presence and/or extend of the disease. Gallium citrate 67 is also used in the diagnosis of abscess and/or focal sites of infection. Scintigraphy using Neoscan® is also called Gallium contrast media. The gallium citrate 67 may be administered intravenously and the readings of the body concentrations are normally carried out between 6 and 120, preferably 48, hours after injection.

"Scintigraphy" is meant to encompass the administration of the substance administered and allowing the readings of the body concentration of said substance.

It has now surprisingly been found that the concomitantly intake or the concomitant presence within the human body, of a substituted 3,5-diphenyl-1,2,4-triazole, as defined further below, may interfere with the distribution pattern of gallium when carrying out scintigraphy, e.g. gallium scintigraphy.

The present invention is therefore directed to a therapeutic treatment removing an excess of iron in the human or animal body whereby said body is undergoing scintigraphy, especially scintigraphy based on gallium, e.g. gallium 67 scintigraphy, and whereby the therapeutic treatment removing an excess of iron is interrupted 2 to 15, e.g. 2 to 10 days prior to the scintigraphy and resumed after the scintigraphic readings.

Preferably, the therapeutic treatment removing an excess of iron is interrupted 2 to 15 days, 2 to 10 days, 2 to 8 days, most preferred 2, 3 4, 5, 6, 7 or 8 days prior to the scintigraphy. This means for example that the therapeutic treatment removing an excess of iron is interrupted 2 to 8 days before the administration of the substance, e.g. gallium 67, administered prior to the readings of the body concentration of said substance, e.g. gallium 67, which allows said readings.

One aspect of the present invention relates to the use of a compound of the formula I

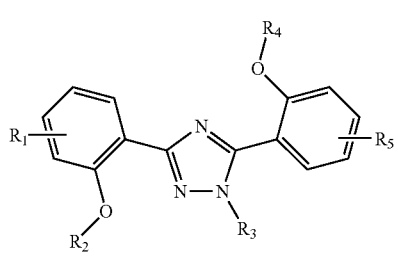

in which
$R_1$, and $R_5$ simultaneously or independently of one another are hydrogen, halogen, hydroxyl, $C_{1-7}$alkyl, halo-$C_{1-7}$alkyl, $C_{1-7}$alkoxy, halo-$C_{1-7}$alkoxy, carboxyl, carbamoyl, N—$C_{1-7}$ alkylcarbamoyl, N,N-di-$C_{1-7}$ alkylcarbamoyl or nitrile;
$R_2$ and $R_4$ simultaneously or independently of one another are hydrogen, unsubstituted or substituted $C_{1-7}$alkanoyl or aroyl, or a radical which can be removed under physiological conditions;
$R_3$ is hydrogen, $C_{1-7}$alkyl, hydroxy-$C_{1-7}$alkyl, halo-$C_{1-7}$alkyl, carboxy-$C_{1-7}$alkyl, $C_{1-7}$alkoxycarbonyl-$C_{1-7}$alkyl, $R_6R_7N$—C(O)—$C_{1-7}$alkyl, unsubstituted or substituted aryl or aryl-$C_{1-7}$ alkyl, or unsubstituted or substituted heteroaryl or heteroaralkyl;
$R_6$ and $R_7$ simultaneously or independently of one another are hydrogen, $C_{1-7}$alkyl, hydroxy-$C_{1-7}$alkyl, alkoxy-$C_{1-7}$alkyl, hydroxyalkoxy-$C_{1-7}$alkyl, amino-$C_{1-7}$alkyl, N—$C_{1-7}$alkylamino-$C_{1-7}$alkyl, N,N-di-$C_{1-7}$alkylamino-$C_{1-7}$alkyl, N-(hydroxy-$C_{1-7}$alkyl)amino-$C_{1-7}$alkyl, N,N-di(hydroxy-$C_{1-7}$alkyl)amino-$C_{1-7}$alkyl or, together with the nitrogen atom to which they are bonded, form an azaalicyclic ring; e.g. 4-[3,5-bis(2-hydroxyphenyl)-[1,2,4]triazol-1-yl]benzoic acid, or a salt thereof;
in the treatment of diseases which cause an excess of iron in the human or animal body or are caused by it, whereby said body is undergoing scintigraphy, especially scintigraphy based on gallium 67; preferably in the form of pharmaceutically acceptable preparations, in particular in a method for the therapeutic treatment of the human body, and to a treatment method of this type.

The definition of the different substituents of the compound of formula I, e.g. halogen, alkyl, halo-$C_{1-7}$alkyl, $C_{1-7}$alkoxy, halo-$C_{1-7}$alkoxy, carbamoyl, $C_{1-7}$alkanoyl, $C_{1-7}$alkoxycarbonyl, aryl, aroyl, aryl$C_{1-7}$alkyl, heterocycloalkyl, azaalicyclyl heteroaryl, heteroaryl-$C_{1-7}$alkyl, N—$C_{1-7}$alkylamino, a radical which can be removed under physiological conditions and salts of compounds of formula I are disclosed in the International Patent Publication WO97/49395 and are incorporated hereby by reference.

Preferably, the invention relates to above described use comprising at least one compound of the formula I in which $R_1$ and $R_5$ simultaneously or independently of one another are hydrogen, halogen, hydroxyl, $C_{1-7}$alkyl, halo-$C_{1-7}$alkyl, $C_{1-7}$alkoxy, halo-$C_{1-7}$alkoxy; $R_2$ and $R_4$ simultaneously or independently of one another are hydrogen or a radical which can be removed under physiological conditions;
$R_3$ is $C_{1-7}$alkyl, hydroxy-$C_{1-7}$alkyl, halo-$C_{1-7}$alkyl, carboxy-$C_{1-7}$alkyl, $C_{1-7}$alkoxycarbonyl-$C_{1-7}$alkyl, $R_6R_7N$—C(O)—$C_{1-7}$alkyl, substituted aryl or aryl-$C_{1-7}$alkyl, substituted by N—$C_{1-7}$ alkylamino, N,N-di$C_{1-7}$ alkylamino or pyrrolidino, or unsubstituted or substituted heteroaryl or heteroaralkyl;
$R_6$ and $R_7$ simultaneously or independently of one another are hydrogen, $C_{1-7}$alkyl, hydroxy-$C_{1-7}$alkyl, alkoxy-$C_{1-7}$alkyl, hydroxyalkoxy-$C_{1-7}$alkyl, amino-$C_{1-7}$alkyl, N—$C_{1-7}$alkylamino-$C_{1-7}$alkyl, N,N-di-$C_{1-7}$alkylamino-$C_{1-7}$alkyl, N-(hydroxy-$C_{1-7}$alkyl)amino-$C_{1-7}$alkyl, N,N-di(hydroxy-$C_{1-7}$alkyl)amino-$C_{1-7}$alkyl or, together with the nitrogen atom to which they are bonded, form an azaalicyclic ring; or a salt thereof; and at least one pharmaceutically acceptable carrier, and to methods for their preparation.

Very particularly preferred the compound of formula I is 4-[3,5-bis(2-hydroxyphenyl)-[1,2,4]triazol-1-yl]benzoic acid or a pharmaceutically acceptable salt thereof. According to any embodiment of the present inventions, a preferred Compound of formula I is 4-[3,5-bis(2-hydroxyphenyl)-[1,2,4]triazol-1-yl]benzoic acid or a pharmaceutically acceptable salt thereof.

In a particular aspect, the present invention relates to the use of a compound of formula I as described above, e.g. 4-[3,5-bis(2-hydroxyphenyl)-[1,2,4]triazol-1-yl]benzoic acid, e.g. or a pharmaceutically acceptable salt thereof, for the preparation of a pharmaceutically acceptable preparation for the treatment of an excess of iron in the human or animal body whereby said body is undergoing scintigraphy, especially scintigraphy based on gallium 67, and whereby the therapeutic treatment removing an excess of iron is interrupted 2 to 10 days prior to the scintigraphy and resumed after the scintigraphic readings.

The present invention pertains to a pharmaceutically acceptable composition comprising a compound of formula I as described above or a pharmaceutically acceptable salt thereof, for the treatment of an excess of iron in the human or animal body whereby said body is undergoing scintigraphy, and whereby the therapeutic treatment removing an excess of iron is interrupted 2 to 10 days prior to the scintigraphy and resumed after the scintigraphic readings.

The present invention relates to a method of diagnostic using scintigraphy, e.g. gallium scintigraphy, wherein when the patient is a patient undergoing Compound of formula I, e.g. 4-[3,5-bis(2-hydroxyphenyl)-[1,2,4]triazol-1-yl]benzoic acid, or a pharmaceutically acceptable salt thereof treatment, said diagnostic method is characterized in that Compound of formula I, e.g. 4-[3,5-bis(2-hydroxyphenyl)-[1,2,4]triazol-1-yl]benzoic acid, or a pharmaceutically acceptable salt thereof treatment is interrupted for a period of 2 to 10 days prior to said method of diagnostic using gallium scintigraphy and resumed after said diagnostic method has been performed, or after the readings.

The invention relates to a medicament package comprising:
(a) a pharmaceutical composition comprising Compound of formula I, e.g. 4-[3,5-bis(2-hydroxyphenyl)-[1,2,4]triazol-1-yl]benzoic acid, or a pharmaceutically acceptable salt thereof, and
(b) printed instructions directing that the pharmaceutical composition comprising Compound of formula I, e.g. 4-[3,5-bis(2-hydroxyphenyl)-[1,2,4]triazol-1-yl]benzoic acid, or a pharmaceutically acceptable salt thereof, is not to be administered to patients 2 to 10 days prior to gallium scintigraphy and the administration of Compound of formula I, e.g. 4-[3, 5-bis(2-hydroxyphenyl)-[1,2,4]triazol-1-yl]benzoic acid, or a pharmaceutically acceptable salt thereof, is resumed after the gallium scintigraphy readings.

The invention also relates to the use of Compound of formula I, e.g. 4-[3,5-bis(2-hydroxyphenyl)-[1,2,4]triazol-1-yl]benzoic acid, or a pharmaceutically acceptable salt thereof, for the manufacture of a medicament for the treatment of iron overload characterized in that Compound of formula I, e.g. 4-[3,5-bis(2-hydroxyphenyl)-[1,2,4]triazol-1-yl]benzoic acid, or a pharmaceutically acceptable salt thereof, is interrupted for a period of 2 to 10 days prior to gallium scintigraphy and resumed after said scintigraphy.

In one embodiment the invention pertains to the use of Compound of formula I for the manufacture of a medicament for the treatment of iron overload wherein said compound is administered daily or according to the manufacturer's instructions to the patient characterized in that if the patient has to undergo scintigraphy, e.g. gallium scintigraphy, the administration of said compound, is interrupted 2 to 10 days prior to the scintigraphy, e.g. gallium scintigraphy and is resumed after said scintigraphy.

By "Compound of formula I" is meant a compound of formula I as mentioned above or a pharmaceutically acceptable salt thereof.

The following patent application WO2004/035026 published on Apr. 29, 2004, provides the description of pharmaceutical preparation, e.g. in the form of a dispersible tablet, comprising a compound of formula I or a pharmaceutically acceptable salt thereof, as active ingredient being present in an amount of about 5 to 40%.

The preferences given above for a compound of formula I in relation to its use equally apply to the preferred compounds of formula I when present in a pharmaceutical preparation, e.g. a dispersible tablet.

It has also surprisingly been found that said substituted 3,5-diphenyl-1,2,4-triazole, e.g. Compound I of formula I, e.g. 4-[3,5-bis(2-hydroxyphenyl)-[1,2,4]triazol-1-yl]benzoic acid, enhances the accumulation of gallium in highly perfused organs, such as the liver, lungs, heart, kidney and brain.

The present invention is also directed to the use of gallium and a gallium uptake enhancer, e.g. a substituted 3,5-diphenyl-1,2,4-triazole, e.g. a Compound of formula I, e.g. 4-[3,5-bis(2-hydroxyphenyl)-[1,2,4]triazol-1-yl]benzoic acid, or a pharmaceutically acceptable salt thereof:
1) to improve tumor imaging;
2) to improve radiotherapy of tumors; and
3) to improve the use of gallium as an adjunct to chemotherapy, e.g. in the treatment cancer, e.g. in the treatment of liver cancer,
4) to treat a disease which is responsive to gallium therapy,
5) to treat a disease which is responsive to Compound I therapy,
6) to treat a disease which is responsive to gallium therapy and to Compound I therapy.

In one embodiment of the invention, the method can improve the uptake of gallium, e.g. of an isotope of gallium, into tumor cells, to permit a total diagnostic or therapeutic dose of the radioisotope to be decreased, so that less then the normal 5-10 mCi adult dose can be administered to an adult.

One aspect of the present invention relates to a combination comprising a compound of the formula I as defined above, e.g. 4-[3,5-bis(2-hydroxyphenyl)-[1,2,4]triazol-1-yl]benzoic acid or a salt thereof; and a gallium.

In further aspect of the invention, the combination is a combined preparation for simultaneous, separate or sequential use in the treatment of a disease which respond to gallium therapy and/or to Compound of formula I, e.g. 4-[3,5-bis(2-hydroxyphenyl)-[1,2,4]triazol-1-yl]benzoic acid, therapy One aspect of the present invention relates to the use of a compound of the formula I as defined above, e.g. 4-[3,5-bis(2-hydroxyphenyl)-[1,2,4]triazol-1-yl]benzoic acid, or a salt thereof, for enhancing the gallium uptake by highly perfused organs; preferably in the form of pharmaceutically acceptable preparations, in particular in a method for diagnosis or for a therapeutic treatment of the human body, and to a diagnostic or treatment method of this type.

The organs are, e.g. simultaneously or substantially concurrently, exposed to the gallium uptake enhancer compound of formula I, e.g. 4-[3,5-bis(2-hydroxyphenyl)-[1,2,4]triazol-1-yl]benzoic acid, and a gallium compound such as a salt containing a stable or unstable isotope.

The gallium uptake enhancer and a gallium compound such as a salt containing a stable or unstable isotope can be administered in the form of a complex between the gallium uptake enhancer and the gallium compound.

The structure of the resulting Ga complex is as described by formula II:

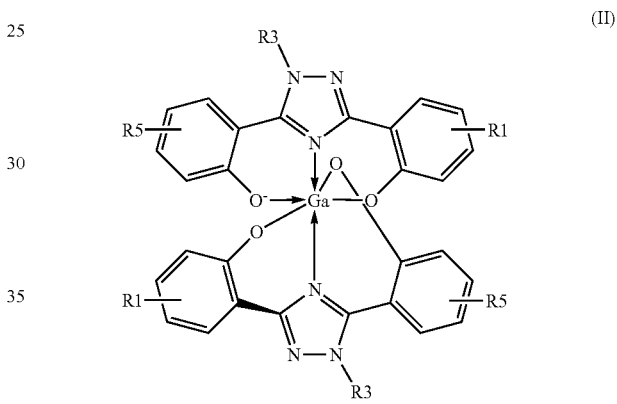

wherein R1 to R5 have the same meaning as in the definition of Compounds of formula I described above. Ga is "Gallium" as defined below, i.e. isotopes of gallium, such as Ga-67, Ga-68, Ga-69, Ga-71, or Ga-72, (where Ga-69 and 71 are stable, and Ga-67, 68, 70 and 72 are unstable), and compounds such as gallium nitrate, gallium citrate, or gallium chloride salts. The arrow represents a bond which is not a covalent bond.

The organ which is exposed to the gallium and the enhancer compound of formula I may have tumor cells, so that uptake of chemotherapeutic amounts of gallium and/or of Compound of formula I into the tumor can be differentially increased, compared to non-tumor cells.

Particular examples of diseases which can be responsive to gallium and/or to Compound of formula I or of tumor cells or tumor types which could be exposed to the gallium and a gallium uptake enhancer are: a liver cancer, e.g. liver adenocarcinoma, hepatocellular carcinoma; sarcoma, myeloma, renal adenocarcinoma, testicular leydig cell tumor, medullary thyroid carcinoma, neuroblastoma, melanoma, colon adenocarcinoma, lung adenocarcinoma, or intraductal breast carcinoma.

The disclosed methods can be used to increase cellular gallium uptake either in vitro or in vivo. For in vivo applications, the gallium and the gallium uptake enhancer are administered to a subject, such as someone who has been diagnosed with a tumor. The gallium may be administered in a therapeutically effective anti-neoplastic amount, when combined with the gallium uptake enhancer.

Alternatively, the gallium may be administered in an amount effective to image the tumor in a gallium scan, when the gallium is administered in combination with the gallium uptake enhancer. For tumor imaging or for diseases responsive to gallium treatment, the gallium and the gallium uptake enhancer can be administered as a complex gallium-gallium uptake enhancer, e.g. as a complex of formula II. For treatment of diseases responsive to gallium treatment and/or to Compound of formula I or Complex of formula II treatment, Compound of formula I can be administered in an amount such as not all Compound of formula I amount will be complexed or bound to gallium.

Combined administration does not require simultaneous administration, but can refer to simultaneous, substantially simultaneous or separate administration. In particular embodiments, the gallium uptake enhancer is administered prior to the gallium, but within a sufficient period of time to enhance uptake by the tissue of interest, e.g. such as the tumor.

Particular embodiments of the method include imaging a tumor with a gallium scan, by administering to a subject an effective amount of a gallium uptake enhancer, such as a compound of formula (I), that increases uptake of gallium by a tumor. A sufficient amount of gallium is also administered to the subject to perform the gallium scan, wherein the sufficient amount of gallium is less than required to perform the gallium scan in the absence of the gallium uptake enhancer. When the method is used to improve imaging of tumors, Ga-67 is a particularly suitable isotope, and 50% or less of the usual dose of 10 millicuries of gallium can be administered to perform the scan. Hence a dose of less than about millicuries of the Ga-67 can be used. The uptake enhancer can also allow the tumor to be imaged much more quickly than in the absence of the enhancer. Hence instead of waiting 36-72 hours to obtain the image, the diagnostic procedure can be performed 24 hours or less after administration of the gallium.

The following definitions will help with an understanding of the terms used in this specification.

A "gallium uptake enhancer" is an agent that increases the amount of gallium in a cell or an organ above the amount that is present in the absence of such a gallium uptake enhancer.

"Gallium" includes isotopes of gallium, such as Ga-67, Ga-68, Ga-69, Ga-71, or Ga-72, (where Ga-69 and 71 are stable, and Ga-67, 68, 70 and 72 are unstable), and gallium compounds such as gallium nitrate, gallium citrate, or gallium chloride salts.

A "gallium scan" is a nuclear medicine imaging technique in which a radioactive isotope of gallium, such as Ga-67, is given to a patient intravenously or by another adequate means of administration. After administration, the gamma emissions are measured with a gamma camera which produces a photographic image that correlates intensity of tissue uptake with darkness of image. The photographic image provides information that is useful for diagnosis and therapeutic assessment.

A "PET scan" is a nuclear medicine imaging technique in which a radioactive isotope of gallium that emits positrons, such as Ga-68, is administered to a patient intravenously. After administration, the positron emissions are measured and the information is used for diagnosis and therapeutic assessment.

A "tumor" is a neoplasm, and includes both benign and malignant tumors. This term particularly includes malignant tumors which can be either solid, e.g. such as a breast, liver, or prostate carcinoma, or non-solid, e.g. such as a leukemia. Tumors can also be further divided into subtypes, such as adenocarcinomas, e.g. of the breast, prostate, lung, or liver cancer, e.g. liver adenocarcinoma, hepatocellular carcinoma; sarcoma, myeloma, renal adenocarcinoma, testicular leydig cell tumor, medullary thyroid carcinoma, neuroblastoma, melanoma, colon adenocarcinoma, lung adenocarcinoma, or intraductal breast carcinoma.

A "therapeutically effective dose" is a dose sufficient to prevent advancement, or to cause regression of the disease, or which is capable of relieving symptoms caused by the disease.

A "mammal" includes both human and non-human mammals. Similarly, the term "subject" includes both human and veterinary subjects.

An animal is a living multicellular vertebrate organism, a category which includes, for example, mammals and birds.

The present invention pertains to a combination comprising a pharmaceutically acceptable preparation of a compound of formula (I) as described above or a pharmaceutically acceptable salt thereof, preferably 4-[3,5-bis(2-hydroxyphenyl)-[1,2,4]triazol-1-yl]benzoic acid or a pharmaceutically acceptable salt thereof and a gallium, e.g. wherein the combination is a combined preparation for simultaneous, separate or sequential use in the treatment of a disease which respond to gallium therapy and/or to Compound of formula I therapy. Gallium is preferably Ga-67.

The invention pertains to said combination wherein the compound of formula I is 4-[3,5-bis(2-hydroxyphenyl)-[1,2,4]triazol-1-yl]benzoic acid or a pharmaceutically acceptable salt thereof.

The invention further pertains to the use of said combination according for the treatment of the human or animal body.

One embodiment of the invention pertains to the use of said combination for the manufacture of a pharmaceutical preparation for use in enhancing the uptake of gallium in highly perfused organs.

The present invention also pertains to the use of the combination as described above for the manufacture of a pharmaceutical preparation for use in gallium scan, e.g. in liver scintigraphy.

In another embodiment the invention pertains to the use of the combination as described above for the manufacture of a medicament for the treatment of a disease which is responsive to gallium treatment and/or to Compound of formula I treatment.

The present invention pertains to a complex of formula II

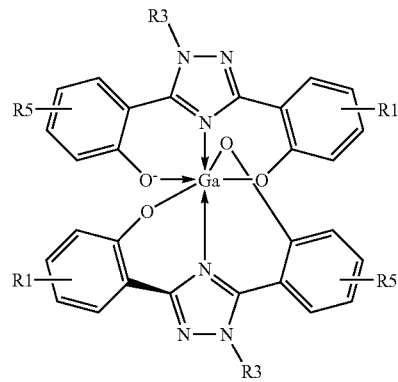

wherein R1, R3 and R5 have the meaning according to Compound of formula I, e.g. wherein R1 is hydroxyl, R3 is phenyl substituted by carboxyl and R5 is hydroxyl.

The invention further pertains to the use of said complex of formula II for the treatment of the human or animal body.

The invention pertains to the use of said complex of formula II for the preparation of a medicament for use in gallium scan, e.g. in liver scintigraphy.

In a further embodiment the invention is to the use of said complex for the preparation of a medicament for the treatment of a disease responsive to gallium therapy and/or to Compound of formula I therapy.

The invention also pertains to a method of diagnostic treatment enhancing the uptake of gallium in highly perfused organs characterized by the administration of the combination as described herein above or of the complex of formula II.

The following Examples show that Compounds of formula I improve gallium uptake in cultured cells, and are intended to illustrate, but not limit, embodiments of the present invention.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

EXAMPLE I

Preparation of a complex of Gallium with a Compound of formula I. e.g. 4-[3,5-bis(2-hydroxyphenyl)-[1,2,4]triazol-1-yl]benzoic acid Such complex may be prepared as follows: 10 mmol of Compound of formula (I) and 5 mmol Gallium(III) acetylacetonate are suspended in 50 ml methanol. 15 mmol of sodium hydroxide, as a 2 mol/L aqueous solution, are added at once under stirring. The clear slightly yellow solution is concentrated, e.g. using a Rotavap. The residue is diluted and re-concentrated several times by the addition of 30 ml portions of ethanol. After addition of the last portion of ethanol, the suspension is filtered and the white solid complex is dried at 100° C./100 Torr for 16 hours.

EXAMPLE II

Determination of the affinity constant of 4-[3,5-bis(2-hydroxyphenyl)-[1,2,4]triazol-1-yl]benzoic acid for gallium The affinity constant of 4-[3,5-bis(2-hydroxyphenyl)-[1,2,4]triazol-1-yl]benzoic acid for Gallium is log $\beta_{120}$=33.8(1) (ionic strength 0.1 M KCl, temperature 25° C.) in water and has been determined by potentiometric measurements according to Steinhauser et al., Eur. J. Inorg. Chem. 2004, pp 4177-4192. Considering the affinity constants of 4-[3,5-bis(2-hydroxyphenyl)-[1,2,4]triazol-1-yl]benzoic acid for other metal ions according to Steinhauser et al., Eur. J. Inorg. Chem. 2004, pp 4177-4192, the ranking according to affinity constants is Fe(III) (highest affinity)>Ga(III)>Al(III)>>Cu(II)>>Zn(II)>>Mg(II)>Ca(II).

The invention claimed is:

1. A complex of formula II

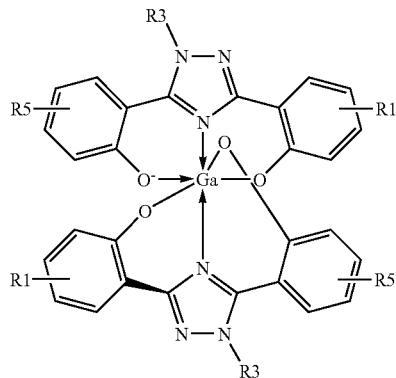

wherein R1 and R5 simultaneously or independently of one another are hydrogen, halogen or hydroxyl; and R3 is hydrogen, $C_{1-7}$alkyl, hydroxy-$C_{1-7}$alkyl, carboxy-$C_{1-7}$alkyl, $C_{1-7}$alkoxycarbonyl-$C_{1-7}$alkyl, $R_6R_7N$—C(O)—$C_{1-7}$alkyl, unsubstituted or substituted aryl or aryl-$C_{1-7}$alkyl, or unsubstituted or substituted heteroaryl or heteroaralkyl.

2. The complex according to claim 1 wherein R1 is hydroxyl, R3 is phenyl substituted by carboxyl and R5 is hydroxyl.

* * * * *